(12) United States Patent
Poo et al.

(10) Patent No.: US 8,162,962 B2
(45) Date of Patent: Apr. 24, 2012

(54) KNOT SETTER

(75) Inventors: Ramon E. Poo, Miami, FL (US); Joseph Lamelas, Miami, FL (US)

(73) Assignee: Miami Instruments LLC, Coral Gables, FL (US)

( * ) Notice: Subject to any disclaimer, the term of this patent is extended or adjusted under 35 U.S.C. 154(b) by 248 days.

(21) Appl. No.: 12/711,866

(22) Filed: Feb. 24, 2010

(65) Prior Publication Data
US 2011/0208214 A1   Aug. 25, 2011

(51) Int. Cl.
A61B 17/04   (2006.01)

(52) U.S. Cl. ........................................................ 606/148

(58) Field of Classification Search .................. 606/139, 606/144, 148, 205, 222, 224, 225; 289/17
See application file for complete search history.

(56) References Cited

U.S. PATENT DOCUMENTS

| | | | |
|---|---|---|---|
| 5,192,287 A | 3/1993 | Fourner et al. | |
| 5,217,460 A * | 6/1993 | Knoepfler | 606/205 |
| 5,250,054 A | 10/1993 | Li | |
| 5,263,958 A | 11/1993 | Deguillebon et al. | |
| 5,281,220 A | 1/1994 | Blake, III | |
| 5,292,327 A * | 3/1994 | Dodd et al. | 606/148 |
| 5,501,698 A | 3/1996 | Roth et al. | |
| 5,512,037 A | 4/1996 | Russell et al. | |
| 5,549,618 A | 8/1996 | Fleenor et al. | |
| 5,562,693 A | 10/1996 | Devlin | |
| 5,628,758 A | 5/1997 | Otten et al. | |
| 5,693,061 A | 12/1997 | Pierce et al. | |
| 5,741,276 A | 4/1998 | Poloyko et al. | |
| 5,741,278 A | 4/1998 | Stevens | |
| 5,797,929 A | 8/1998 | Andreas et al. | |
| 5,827,300 A | 10/1998 | Fleega | |
| 6,045,561 A | 4/2000 | Marshall et al. | |
| 6,511,488 B1 | 1/2003 | Marshall et al. | |
| 6,517,552 B1 * | 2/2003 | Nord et al. | 606/144 |
| 6,723,107 B1 | 4/2004 | Skiba et al. | |
| 6,773,434 B2 | 8/2004 | Ciarrocca | |
| 6,860,890 B2 | 3/2005 | Bachman et al. | |
| 6,866,673 B2 | 3/2005 | Oren et al. | |
| 6,936,054 B2 | 8/2005 | Chu | |
| 2003/0083675 A1 | 5/2003 | Marshall et al. | |
| 2003/0220659 A1 | 11/2003 | Schmieding et al. | |
| 2006/0009791 A1 | 1/2006 | Oren et al. | |
| 2006/0161183 A1 | 7/2006 | Sauer | |
| 2006/0293700 A1 | 12/2006 | Dana et al. | |

OTHER PUBLICATIONS

Notification of Transmittal of the International Search Report and the Written Opinion of the International Searching Authority issued Apr. 19, 2011 under Application No. PCT/US11/026043 (8 pages).

* cited by examiner

*Primary Examiner* — Julian Woo

(74) *Attorney, Agent, or Firm* — Novak Druce + Quigg LLP

(57) ABSTRACT

A surgical knot setter includes an elongated shaft having a long axis and proximal and distal portions. A tip is provided at the distal end of the shaft. The tip has a loop with an interior loop opening and a gate opening for permitting ingress and egress of a suture into the loop opening. The loop is laterally offset from the long axis and distal to the distal end of the shaft, such that the loop is laterally and longitudinally offset from the distal end of the shaft. A closure is provided for selectively opening and closing the gate opening between open and closed positions to selectively permit or prevent the suture from passing through the gate opening. An actuator moves the closure between the open and closed positions. A method for tying suture knots is also disclosed.

2 Claims, 14 Drawing Sheets

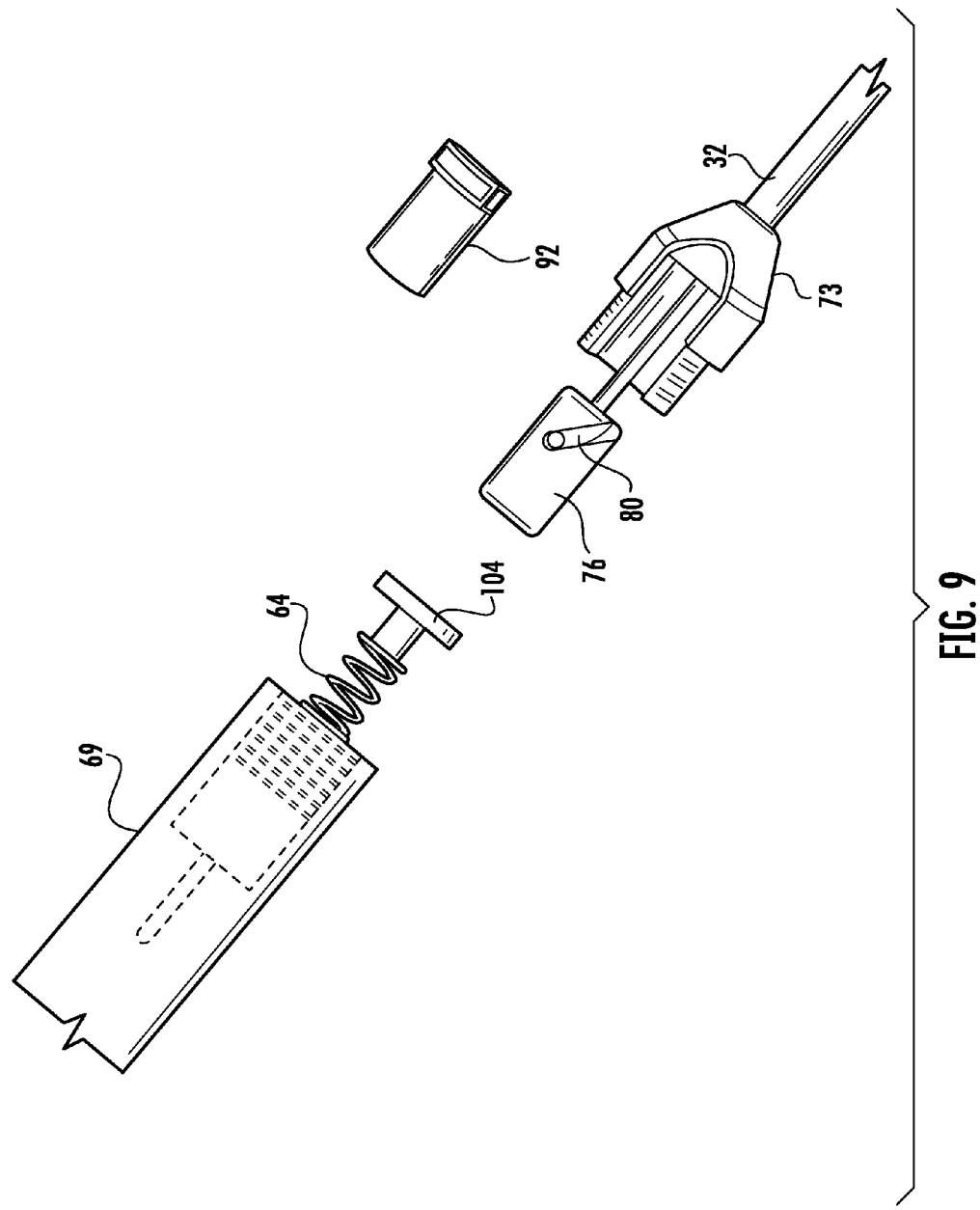

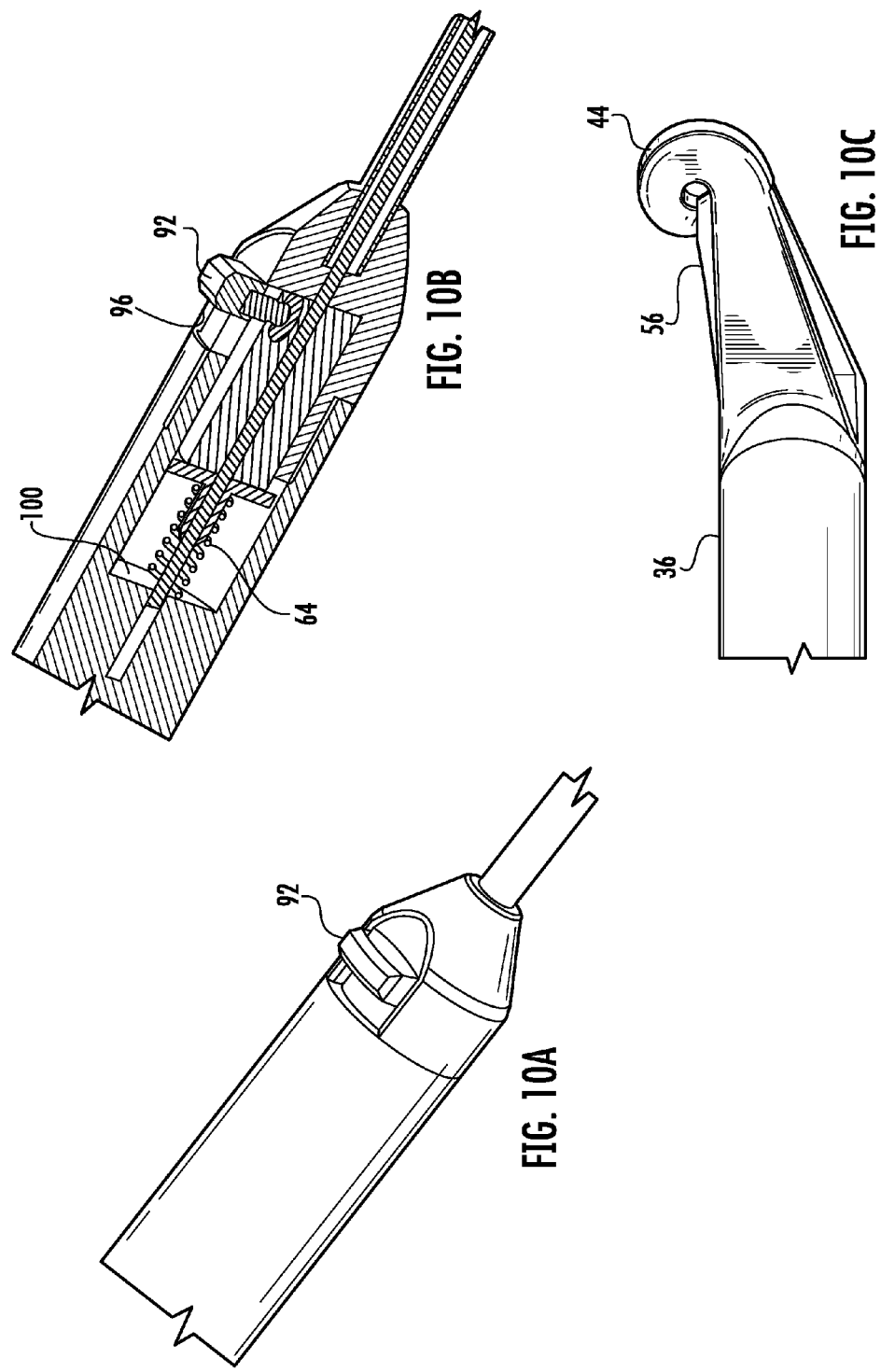

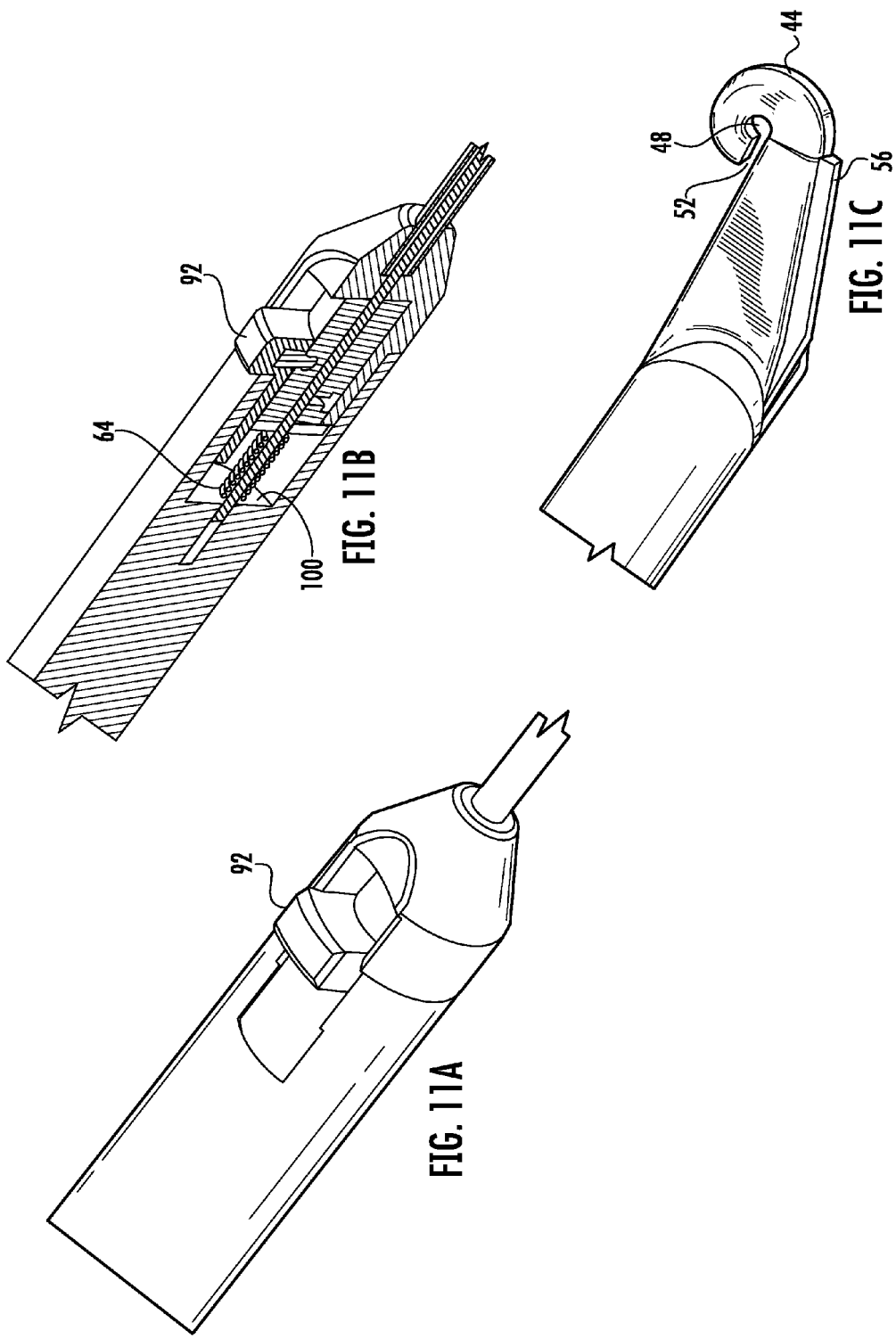

KNOT SETTER

BACKGROUND OF THE INVENTION

The tying of suture knots is a time consuming and tedious part of the surgical process. Multiple knots must be tied to place a suture, sometimes four or more knots per suture, and multiple sutures, sometimes numbering in the hundreds, must be tied during some surgeries. Various devices have been used to assist the surgeon in seating the surgical knots.

SUMMARY OF THE INVENTION

A surgical knot setter has an elongated shaft having a long axis and proximal and distal portions and a tip at the distal portion of the shaft. The tip has a loop with an interior loop opening and a gate opening for permitting ingress and egress of a suture into the loop opening. The loop is laterally offset from the long axis of the shaft and distal to the distal end of the shaft, whereby the loop is laterally and longitudinally offset from the distal end of the shaft. A closure is provided for selectively opening and closing the gate opening between open and closed positions to selectively permit or prevent the suture from passing through the gate opening. An actuator moves the closure between the open and closed positions.

A handle is provided at the proximal end of the shaft. A portion of the actuator is provided in the handle. A portion of the actuator can be aligned with the loop and with the shaft. The shaft can be cylindrical.

The closure can be pivotally connected to the tip and operation of the actuator can cause pivoting of the closure between open and closed positions. The closure can be pivotally mounted to an exterior portion of the tip. The tip can have an interior channel and the closure can be pivotally mounted within the channel.

The tip can have a guide surface for directing the suture into the gate opening. The guide surface can extends from a side of the shaft to the loop.

Biasing can be provided for biasing the closure to the closed position. A portion of the actuator can operate against the biasing to move the closure to the open position.

The elongated shaft can be hollow and can have a drive shaft within the elongated shaft. The elongated shaft can be connected to the closure and to a crank, such that rotation of the crank rotates the drive shaft and the closure. A spiral groove can be provided in the crank and a pin in the groove. The pin is connected to a trigger, such that movement of the trigger moves the pin to contact the spiral groove and rotate the crank and drive shaft.

A method for tying knots with sutures, includes the steps of: providing a surgical knot setter, comprising an elongated shaft having a long axis and proximal and distal portions; a tip at the distal end of the shaft, the tip having a loop having an interior loop opening and a gate opening for permitting ingress and egress of a suture into the loop opening, the loop being laterally offset from the long axis and distal to the distal end of said shaft, whereby the loop is laterally and longitudinally offset from the distal end of the shaft; a closure for selectively opening and closing the gate opening between open and closed positions to selectively permit or prevent the suture from passing through the gate opening; and an actuator for moving the closure between the open and closed positions; positioning the actuator to cause the closure to move to the open position; moving a suture through the gate opening into the interior opening of the loop; operating the actuator to cause the closure to move to the closed position; tying the suture knot and moving the loop to set the suture knot in position; operating the actuator to move the closure to the open position; and, removing the loop from the suture by passing the suture through the gate opening.

BRIEF DESCRIPTION OF THE DRAWINGS

There is shown in the drawings embodiments which are presently preferred, it being understood, however, that the invention can be embodied in other forms without departing from the spirit or essential attributes thereof.

FIG. 9 is an exploded perspective view of an actuator assembly, partially in phantom.

FIGS. 10(A)-(C) are respectively a perspective view of a proximal portion (10A), a cross section of the proximal portion (10B), and a perspective view of a distal tip portion (10A), showing the actuator and tip assembly in a first mode of operation.

FIGS. 11(A)-(C) are respectively a perspective view of a proximal portion (11A), a cross section of the proximal portion (11B), and a perspective view of a distal tip portion (11C), showing the actuator and tip assembly in a second mode of operation.

DETAILED DESCRIPTION OF THE INVENTION

Figure 1:
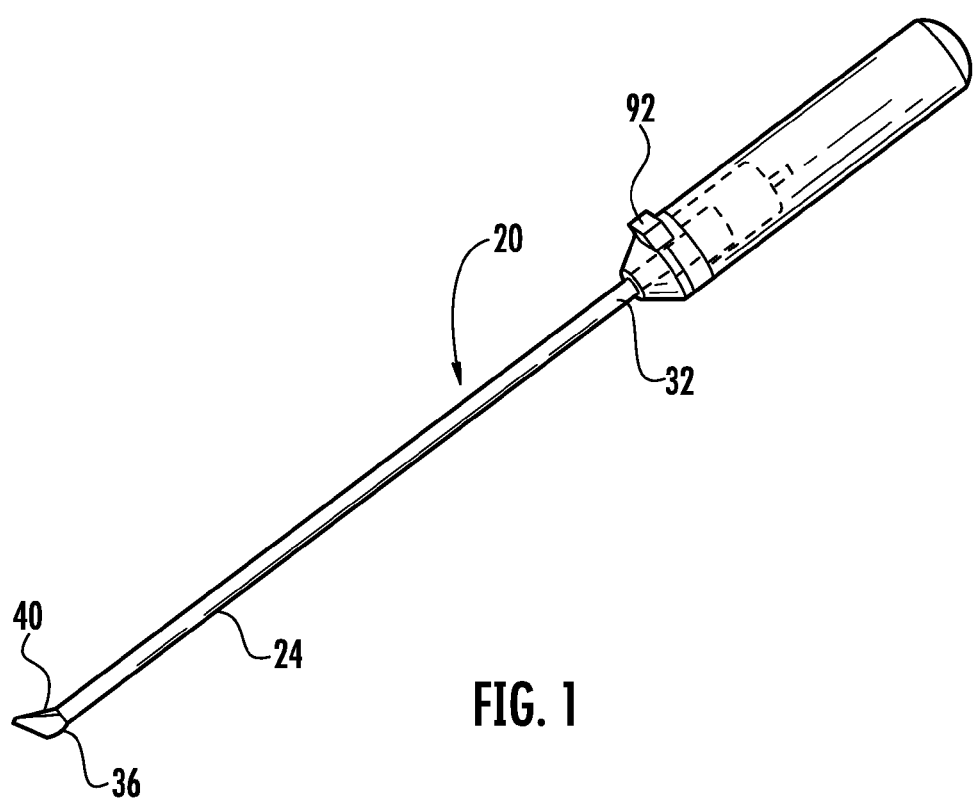
FIG. 1 is a perspective view, partially in phantom, of a knot setter according to the invention.
Figure 2:
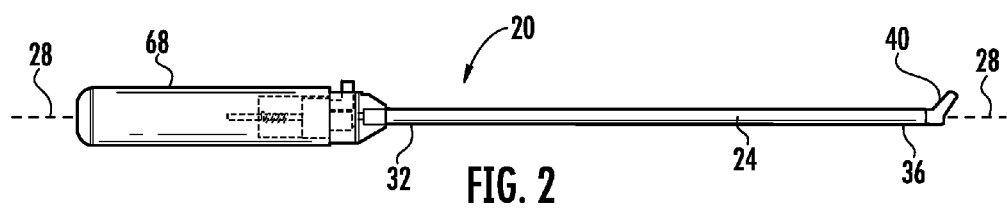
FIG. 2 is side elevation, partially in phantom.
Figure 3:
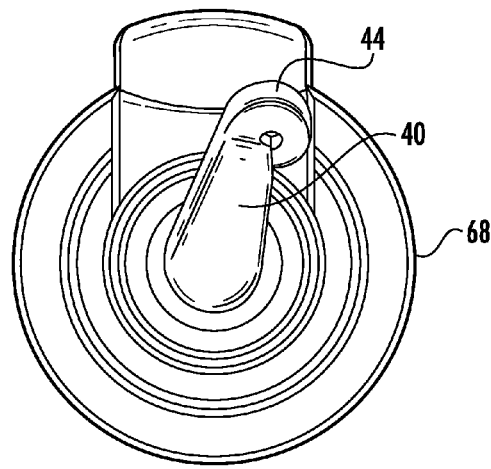
FIG. 3 is a front elevation.
Figure 4:
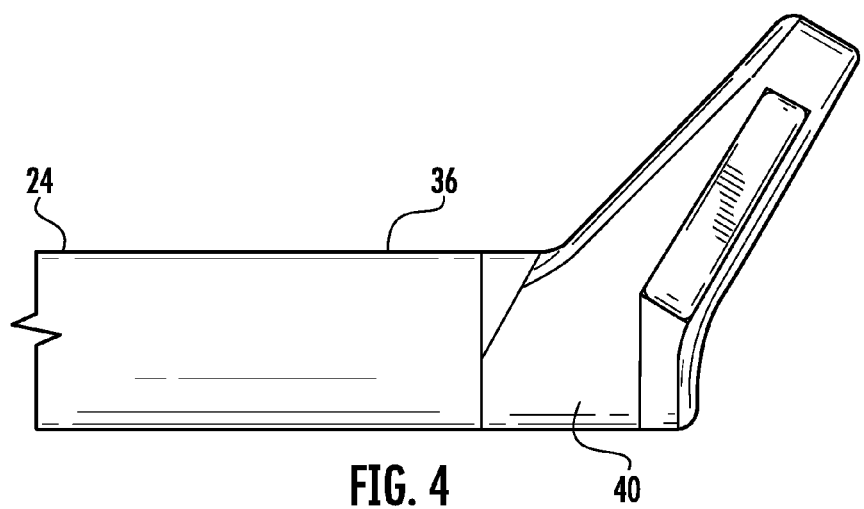
FIG. 4 is a side view of a tip portion.

There is shown in FIGS. 1-15 a knot setter 20 according to the invention. The knot setter 20 has an elongated shaft 24 having a long axis 28 and proximal end 32 and distal end 36. A tip portion 40 is provided at the distal end 36 of the shaft 24. The tip 40 has a loop 44 defining an interior loop opening 48 and a gate opening 52 permitting ingress and egress of a suture into the loop opening 48. The loop 44 is laterally offset from the long axis 28 of the elongated shaft 24, and is longitudinally distanced from the distal end 36 such that the loop 44 is laterally and longitudinally offset from the distal end 36 of the elongated shaft 24. The loop 44 can have any shape or size suitable for retaining the suture, but sharp edges which could damage tissue or cut the suture should be avoided. A closure 56 is provided for selectively opening and closing the gate opening 52 between open and closed positions to selectively permit or prevent the suture from passing through said gate opening 52. An actuator assembly 60 moves the closure 56 between the open and closed positions. The closure 56 in one embodiment remains in the closed position until the actuator assembly 60 is manipulated to move the closure 56 to the open position, and is automatically returned to the closed position when the actuator is released. The surgeon thereby does not have to manipulate the actuator to close the loop around the suture or to retain the suture in the loop.

The actuator assembly 60 can include biasing which biases the closure 56 to the closed position, such that the surgeon can tie multiple knots while the suture remains secure in the loop 44. The actuator assembly 60 can include a spring 64 to bias the closure 56 to the closed position. A handle 68 can be provided and can be connected to the elongated shaft 24. The handle 68 can be a single piece or can comprise multiple pieces such as proximal piece 69 and distal piece 73, which can be secured together by suitable connecting structure such as cooperating threads 75. The elongated shaft 24 can have an open interior through which extends a drive shaft 72. The drive shaft 72 can be secured to a crank 76 as by a set screw 78. The crank 76 can be rotatably mounted in an interior opening 74 of the handle 68. The crank 76 can have a spiral groove 80 formed in an outer surface 84 thereof and extending longitudinally and radially around the surface 84. A pin 88 is fixed to the underside of a trigger 92. The trigger 92 is slidably mounted in a slot 96 formed in the handle 68 and opening to the exterior from the interior opening 74. The pin 88 extends into the groove 80 on the crank 76. Movement of the trigger 92 within the slot 96 will cause the pin 88 to move through the groove 80, and as the pin 88 strikes the sides of the spiral groove 80 the pin 88 will cause rotation of the crank 76. Rotation of the crank 76 will cause rotation of the drive shaft 72. The drive shaft 72 at a distal end thereof is connected to the closure 56, so that rotation of the drive shaft 72 will cause rotation of the closure 56 between the open and the closed positions.

The spring 64 can be positioned in a spring seat 100 provided in the interior opening 74 of the handle 68, and can act on a spring slide 104 that is slidably mounted on the drive shaft 72 and acts on the crank 76 to bias the crank 76 and trigger 92 forward, and thereby the drive shaft 72 and closure 56 to the closed position. In this manner the physician does not have to maintain pressure on the trigger 92 in order to retain the suture in the loop opening 48 of the loop 44. Other constructions for opening and closing the closure 56 and for biasing the closure 56 are also possible. A cable or other structure can take the place of crank shaft 72. Motorized or electrically operated actuators for the closure 56 are also possible. Operation of the trigger 92 causes movement of the closure from the closed position (FIGS. 10A-C) to the open position (FIG. 11A-C).

Figure 5:
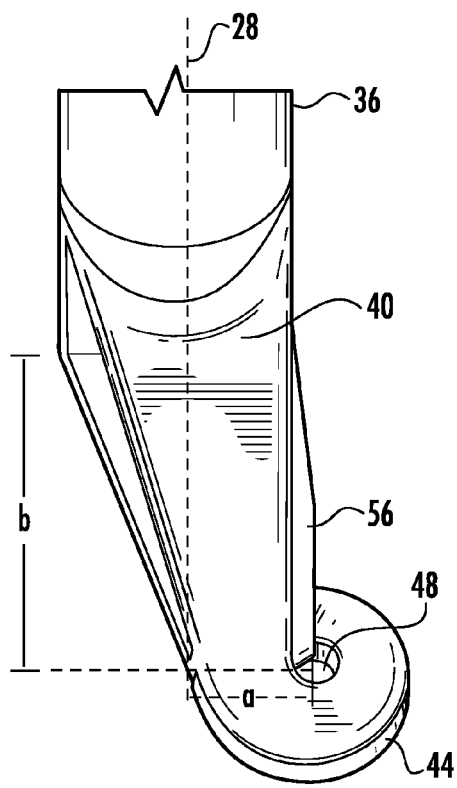
FIG. 5 is a top plan view of a tip portion.
Figure 6:
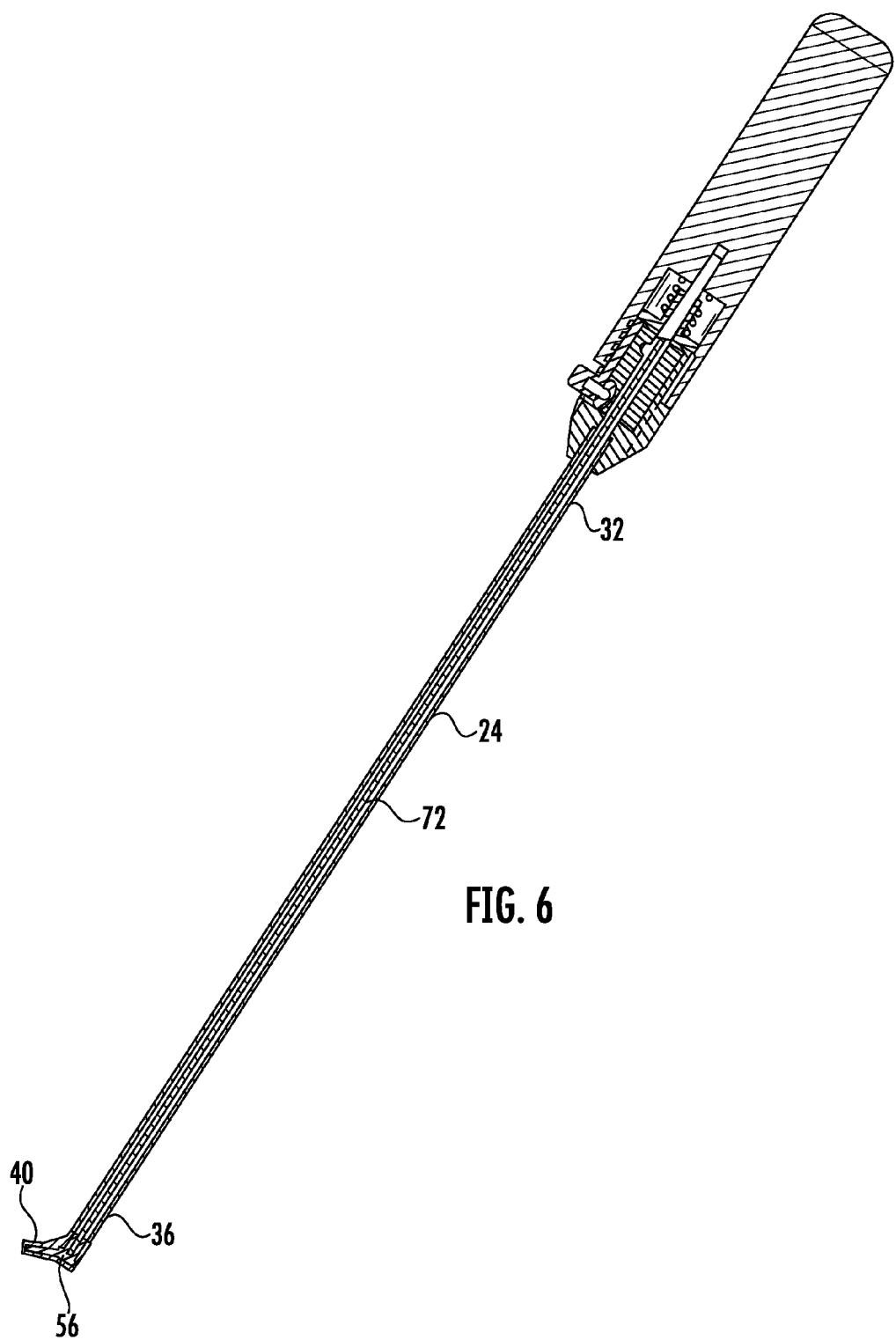
FIG. 6 is a cross section of a knot setter according to the invention.
Figure 7:
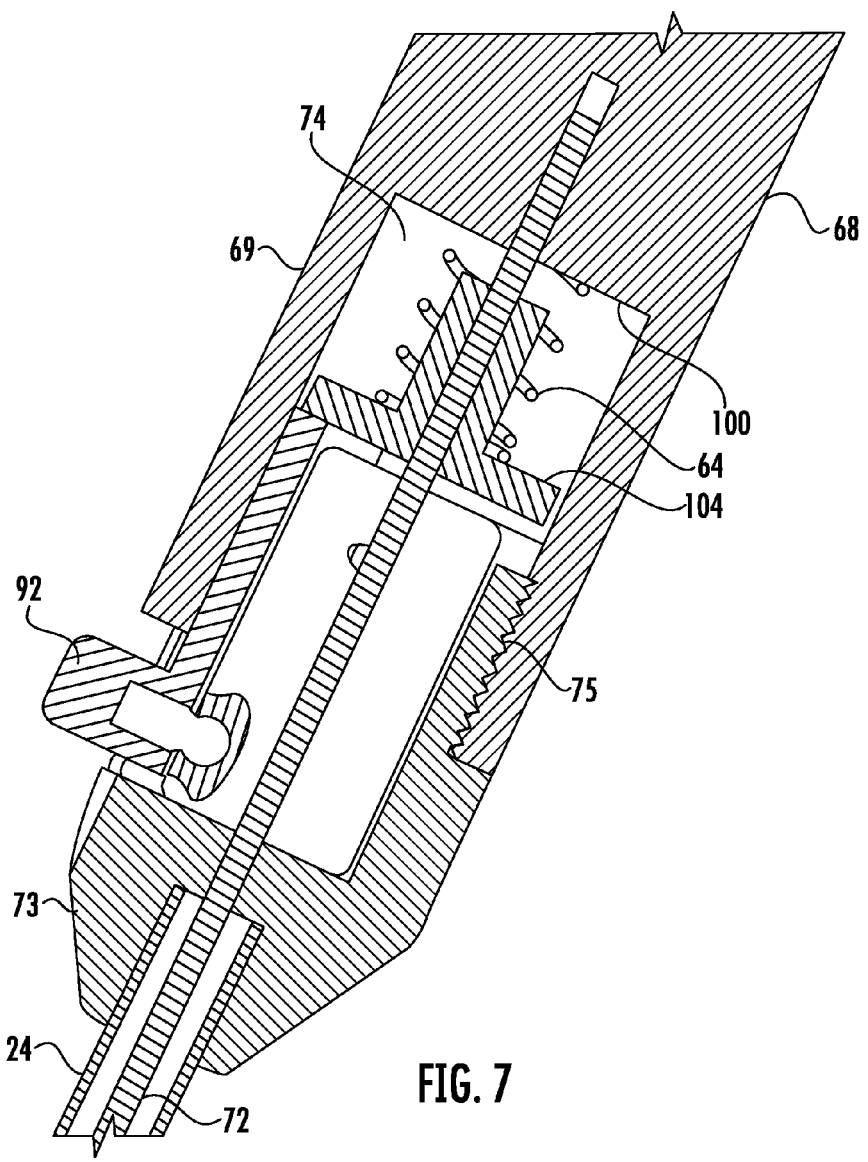
FIG. 7 is an enlarged cross section of a proximal portion of a knot setter.
Figure 8:
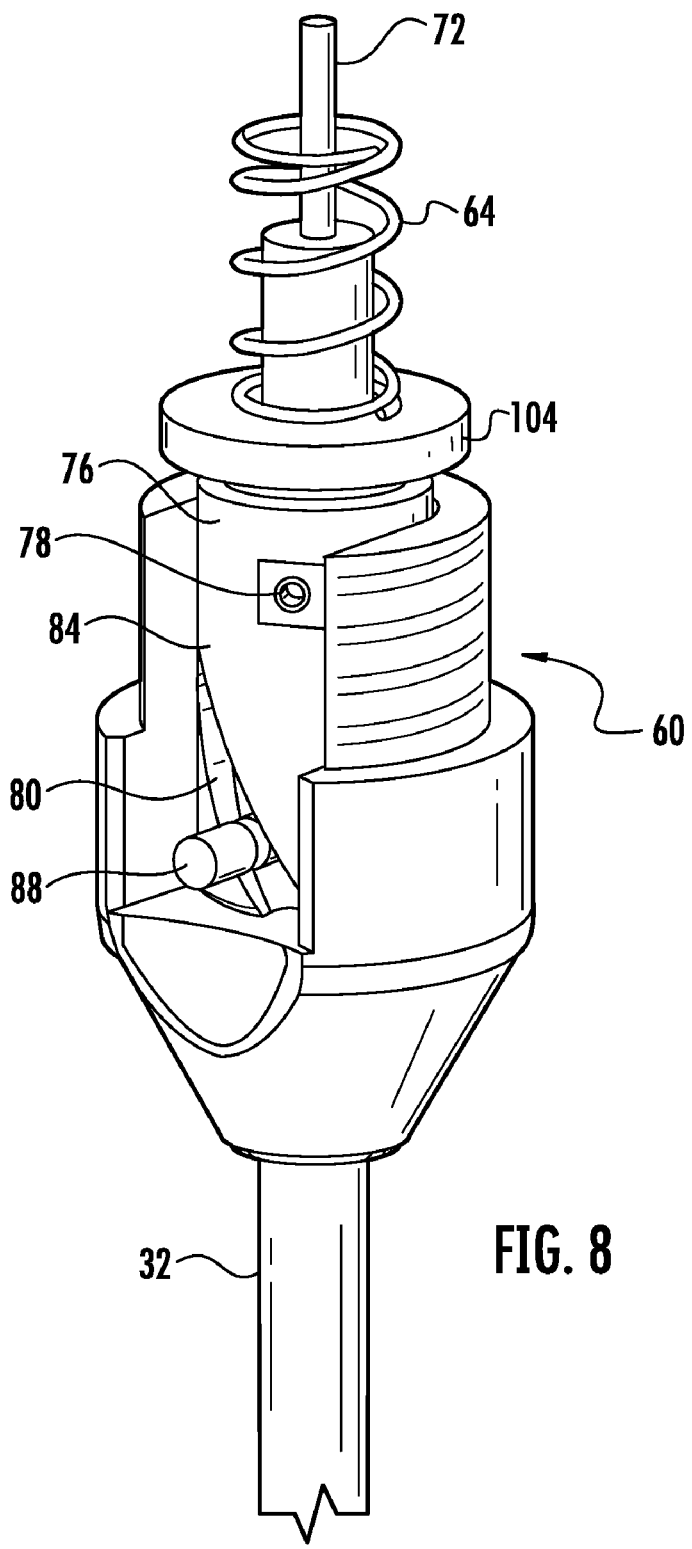
FIG. 8 is a perspective view of an actuator assembly.

In one configuration, the center of the loop 44 is laterally offset from the longitudinal axis 28 of the elongated shaft 24 a distance "a" (FIG. 5). In one embodiment, the distance "a" exceeds the radius of the shaft 24. In another embodiment, the center of the loop 44 is offset by a distance "a" that exceeds the diameter of the shaft 24. The loop 44 can be longitudinally spaced from the distal end 36 of the shaft 24 a distance "b" (FIG. 5). The distance "b" is preferably greater than the diameter of the shaft 24. The trigger 92 can be angularly aligned with the loop 44 so that the surgeon has knowledge of the position of the loop 44 even when it is obscured from view by knowing only the angular position of the trigger 92. Other structure can be provided on the shaft 24 or the handle 68 and angularly aligned with the loop 44 to assist in determining the angular position of the loop 44.

The elongated shaft 24 can have varying lengths and diameters. It is possible to provide different sizes of knot setters according to the invention for different surgical settings where different lengths and configurations of the shaft 24, tip 40 and loop 44 are desirable. The elongated shaft 24 should be smooth at least in areas prone to touch the suture so as to avoid cutting or abrading the suture. The shaft 24 can be cylindrical in shape for this purpose. The tip 40 is configured such that there is a smooth sliding surface 110 leading to the loop opening 48, so that the suture will be directed into the loop opening 48 when the tip 40 is moved gently against the suture and the closure 56 is in the open position.

Figure 14:
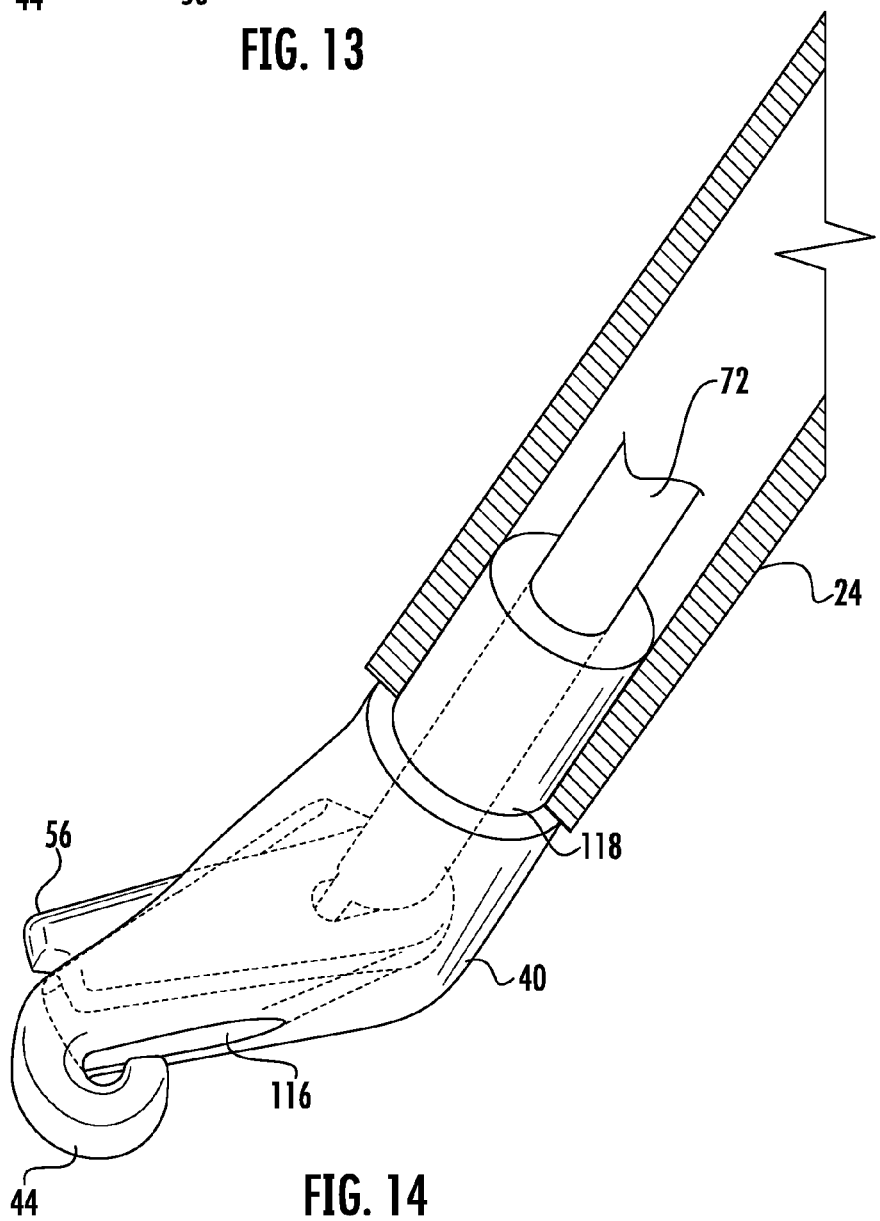
FIG. 14 is a perspective view of a tip portion, partially in phantom, in a first mode of operation.
Figure 15:
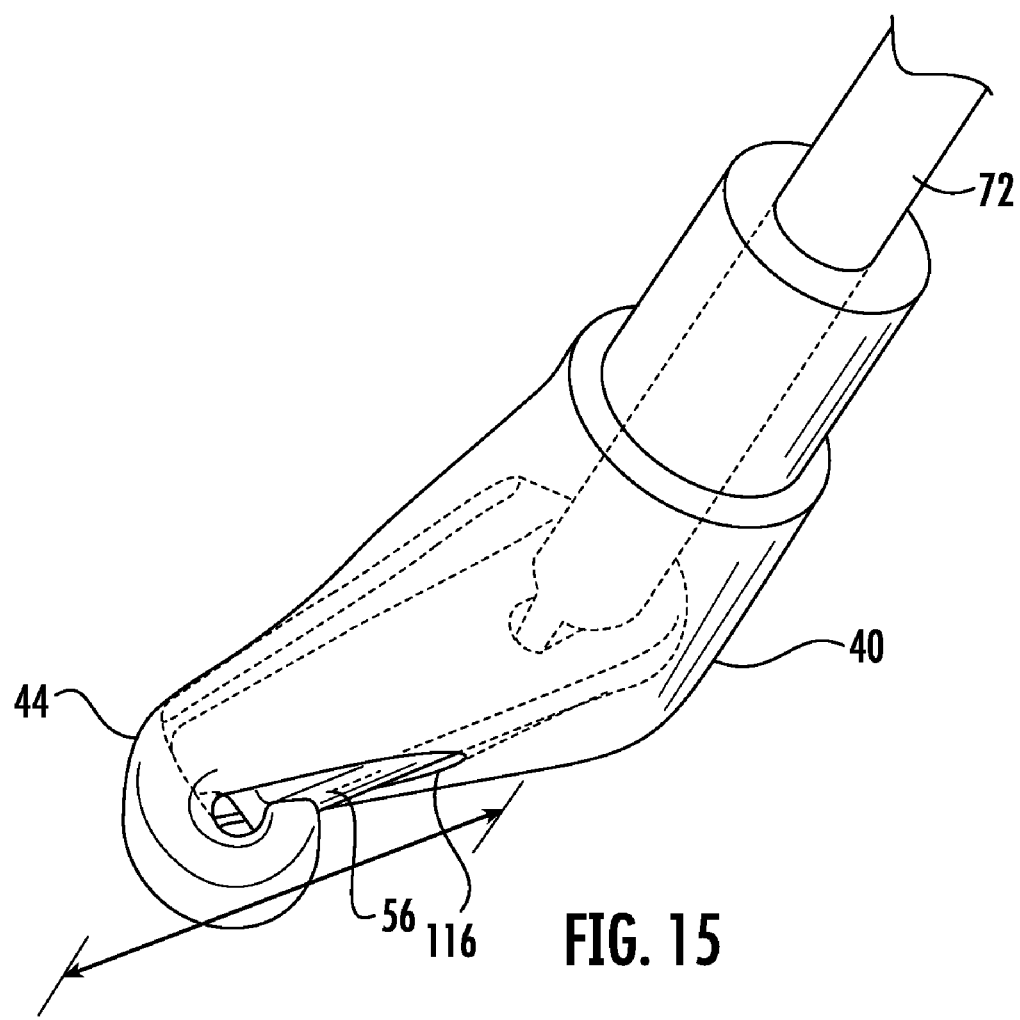
FIG. 15 is a perspective view of a tip portion, partially in phantom, in a second mode of operation.

Different configurations of the tip 40 are possible. In the configuration shown the closure 56 can extend through a slot 116 formed in the tip to close the loop 44 (FIG. 14). The closure 56 is moved through the slot 116 to open the loop 44. The closure 56 is returned to the closed position by operation of the actuator, such as by releasing of the trigger 92 to permit the spring 64 to act on the crank 76 and thereby the drive shaft 72 to move the closure 56 through the slot 116 and close the loop 44 (FIG. 15). In another configuration the closure is positioned adjacent to the tip on a distal side of the tip 40, and is not positioned in a slot. The closure in this embodiment has a concave surface which mates with a convex distal surface on the tip 40 to permit relative pivoting. This is necessary given the angle between the crank shaft 72 and the closure 56.

The knot setter of the invention can be made from a variety of different materials, such as surgical grade stainless steels and plastics. Barium sulfate or other radio opaque material can be applied to or incorporated into these materials in order that the materials can be precisely located in the body.

Figure 12A:
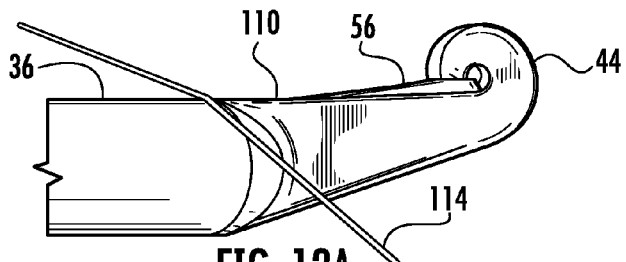
FIGS. 12(A)-(D) are side elevations of a distal tip portion illustrating a method of placing a suture knot according to the invention.
Figure 12B:
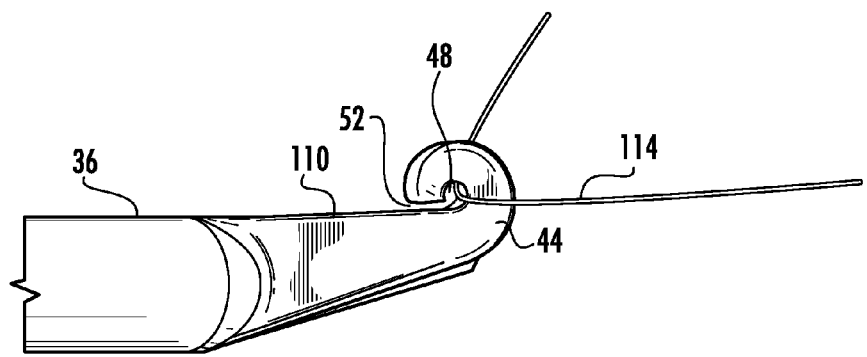
Figure 12C:
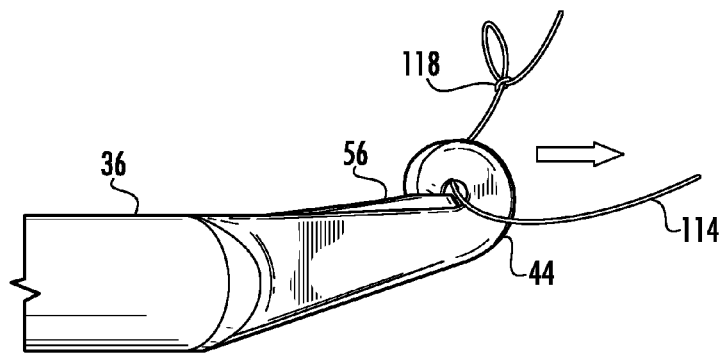
Figure 12D:
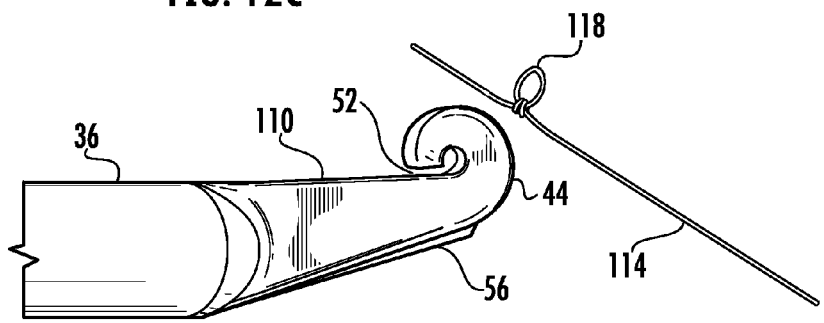
Figure 13:
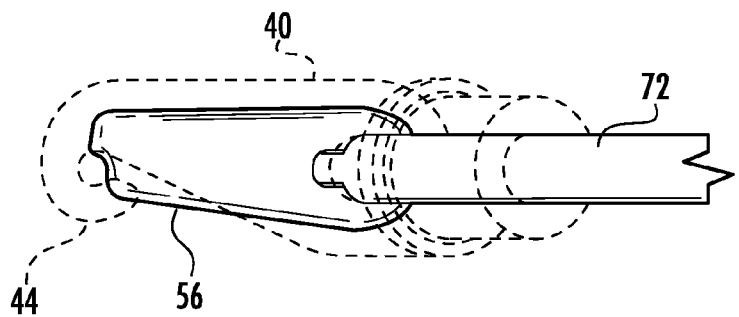
FIG. 13 is a top plan view, partially in phantom, illustrating a tip portion.

Operation of the knot setter is shown in FIGS. 12(A)-(D). The tip 40 of the knot setter 20 is positioned adjacent a suture 114 (FIG. 12A). The closure 56 is moved to the open position by operation of the trigger 92. The loop 44 is placed adjacent to the suture 114, and the position of the trigger 92 can be used to determine the position of the loop 44 if it cannot be seen. The guide surface 110 assists in guiding the suture into the opening 48 of the loop 44 (FIG. 12B). The trigger 92 is then released to permit the closure 56 to move to the closed position under the bias of spring 64. A knot 118 is then tied (FIG. 12C). The knot 118 can then be pushed into the body or "set", and the closure 56 is opened such that the loop 44 can be removed from around the suture 114 and the knot setter 20 can be removed from the patient's body (FIG. 12D).

Figure 16:
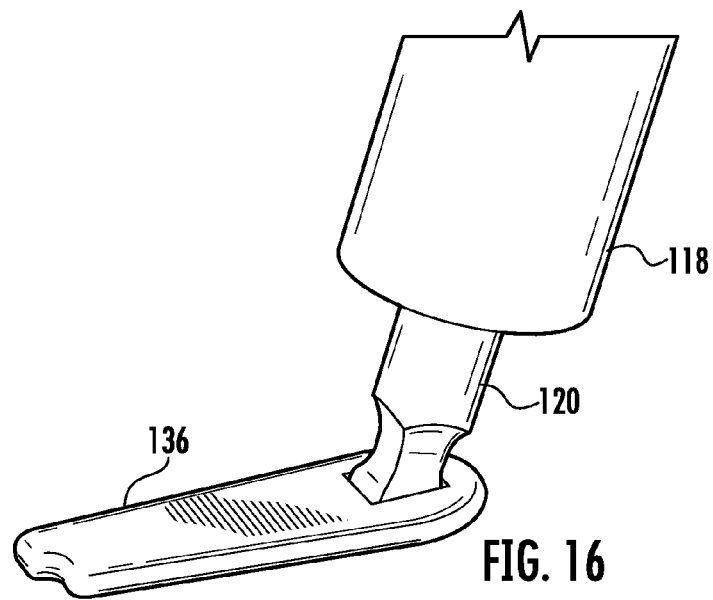
FIG. 16 is a perspective view of an alternative closure and drive shaft design.
Figure 17:
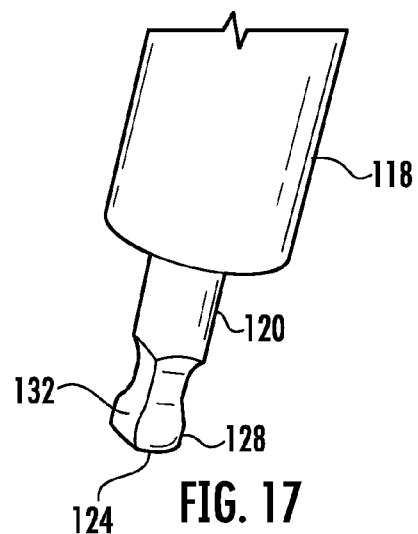
FIG. 17 is a perspective view of an alternative drive shaft.
Figure 18:
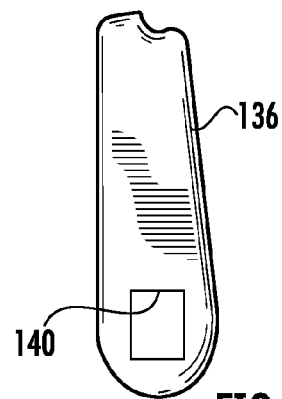
FIG. 18 is a front elevation of an alternative closure.
Figure 19:
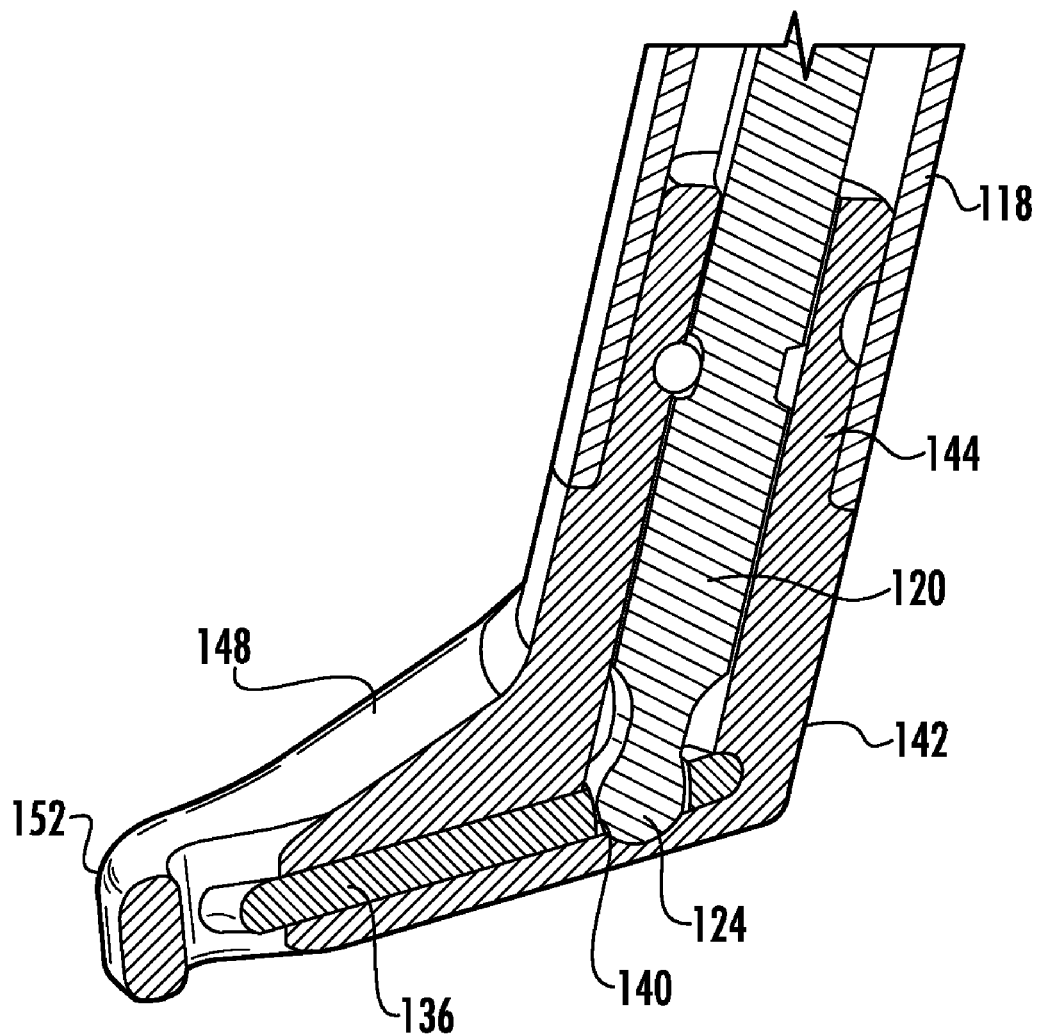
FIG. 19 is a cross section of a tip having the alternative closure and drive shaft.

FIGS. 16-19 illustrate an alternative embodiment in which an elongated shaft 118 encloses a drive shaft 120. The drive shaft 120 has a protrusion 124 for engaging the closure 136. The closure 136 has a rectangular opening 140 that can be a square in outside configuration. The protrusion 124 has linear edges 128 dimensioned and positioned to fit within the rectangular opening 140, as shown in FIG. 16. Rounded side portions 132 provide for rotation of the protrusion 124 within the rectangular opening 140, as shown in FIG. 19. The closure 136 can be provided within a tip portion 142 at a loop extension 148 and can be manipulated to close the loop 152. A neck 144 of the tip 142 can be provided to mate with the elongated shaft 118.

This invention can be embodied in other forms without departing from the spirit or essential attributes thereof and, accordingly, reference should be had to the following claims rather than the foregoing specification as indicating the scope of the invention.

We claim:

1. A surgical knot setter, comprising:
an elongated shaft having a long axis and proximal and distal portions;

a tip at the distal portion of said shaft, said tip having a loop with an interior loop opening and a gate opening for permitting ingress and egress of a suture into the loop opening, said loop being laterally offset from the long axis of the shaft and distal to the distal end of the shaft, whereby the loop is laterally and longitudinally offset from the distal end of the shaft;

a closure for selectively opening and closing the gate opening between open and closed positions to selectively permit or prevent said suture from passing through said gate opening; and, an actuator for moving said closure between said open and closed positions, wherein the elongated shaft is hollow and further comprising a drive shaft within the elongated shaft, said elongated shaft being connected to the closure and to a crank, rotation of the crank rotating the drive shaft and the closure.

2. The knot setter of claim 1, further comprising a spiral groove in the crank and a pin in the groove, the pin being connected to a trigger, movement of the trigger moving the pin to contact the spiral groove and rotate the crank and drive shaft.

* * * * *